United States Patent [19]

Auerbach

[11] 4,405,323
[45] Sep. 20, 1983

[54] SANITARY NAPKIN

[76] Inventor: Sidney Auerbach, 246 W. End Ave., New York, N.Y. 10023

[21] Appl. No.: 299,813

[22] Filed: Sep. 8, 1981

[51] Int. Cl.³ .......................................... A61F 13/20
[52] U.S. Cl. .................................................. 604/285
[58] Field of Search .................. 128/263, 270, 285; 604/11, 14–16, 18, 285, 286

[56] References Cited
U.S. PATENT DOCUMENTS

| | | | |
|---|---|---|---|
| 3,139,886 | 7/1964 | Tallman et al. | 128/263 |
| 3,902,493 | 9/1975 | Baier et al. | 128/270 |
| 4,271,835 | 6/1981 | Conn et al. | 128/270 |
| 4,308,867 | 1/1982 | Roseman et al. | 128/270 |
| 4,309,997 | 1/1982 | Donald | 128/270 |
| 4,317,447 | 3/1982 | Williams | 128/270 |

*Primary Examiner*—C. Fred Rosenbaum
*Attorney, Agent, or Firm*—Anthony H. Handal; Michael N. Meller

[57] ABSTRACT

A tampon (10) designed to eliminate the hazards of toxic shock syndrome or dysmenorrhea by incorporating an antibacterial agent (or agent effective against other microorganisms) into the tampon (10). The antibacterial agent suspended in an adhesive is coated onto a cylindrical insert of absorptive material (12), a tubular applicator container (22), and a plunger (26). On contact with body fluids the antibacterial agent disperses, preventing development of the organisms which produce the toxins which cause toxic shock syndrome.

7 Claims, 4 Drawing Figures

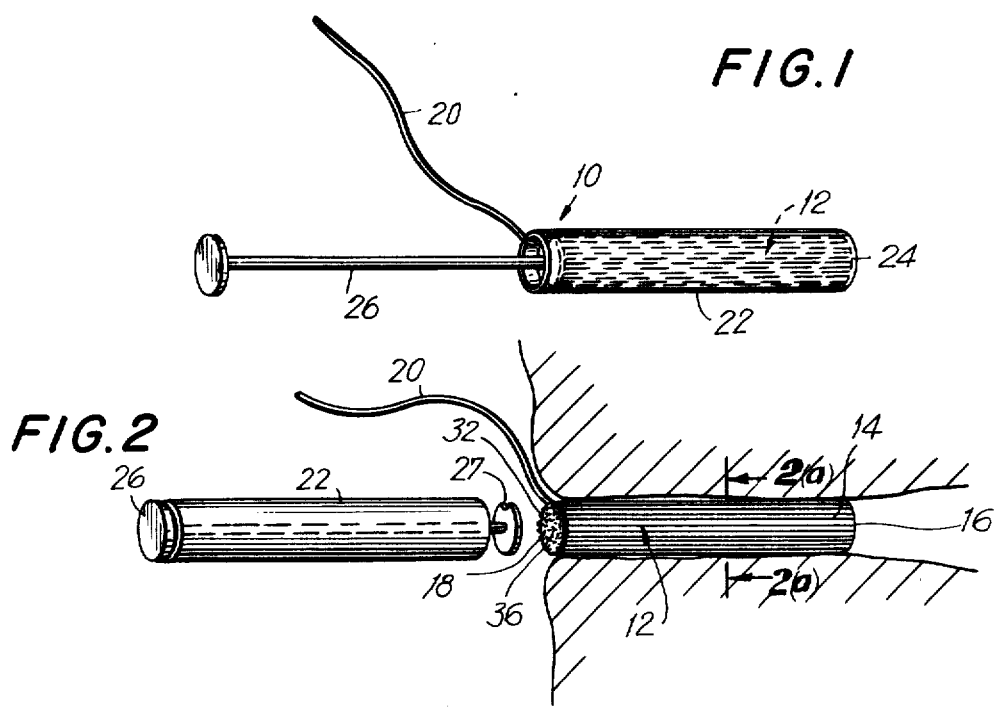
FIG.1
FIG.2
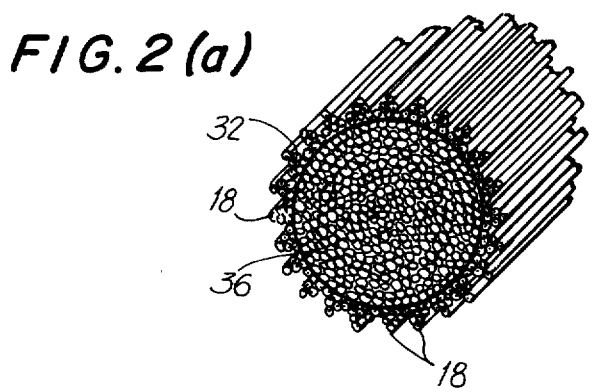
FIG.2(a)
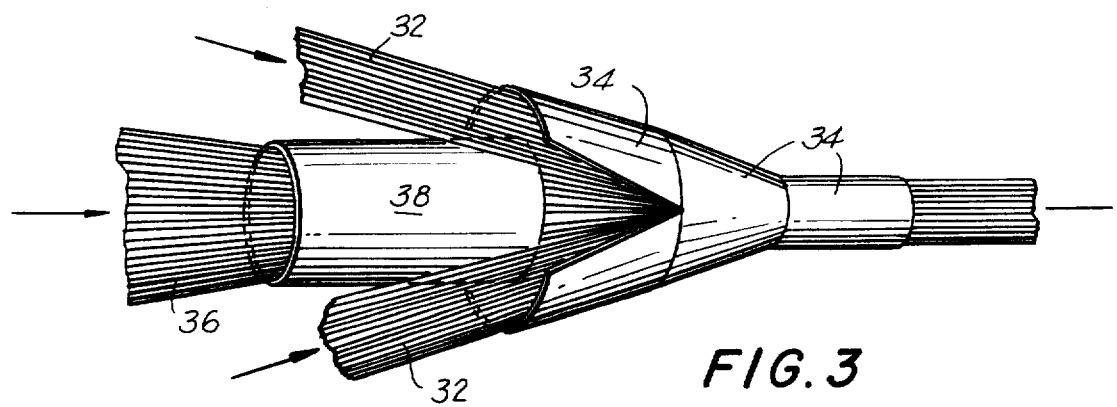
FIG.3

४,४०५,३२३

SANITARY NAPKIN

TECHNICAL FIELD

The invention relates to sanitary napkins of the tampon type which are positioned within the vaginal vault during menstruation, and to other types of tampons used in surgical procedures at other body sites, to prevent or diminish the tendency of pathogenic organisms to cause toxic shock syndrome and dysmenorrhea.

BACKGROUND ART

Recently, the attention of the medical community has been focused upon toxicity problems associated with the use of tampons. Generally, the problem arises as an infection due to Staphylococcus aureaus in the vagina in menstruating women who are using tampons.

Medical authorities have suggested dealing with the problem by a number of techniques. These include discontinuing the use of tampons, discontinuing the use of tampons which are inserted with syringe type mechanical devices and/or alternating the use of inserted tampons with externally used absorbtive feminime napkins.

DISCLOSURE OF INVENTION

Vagina infections caused by staphylococcus aureus may result in a condition known as "toxic shock syndrome". As a result of my work in the development of antiseptic and related agents, I have been led to the conclusion that toxic shock syndrome is caused by toxins produced by the staphylococci which are normally resident, without harm, in perhaps ten percent of the female population. These staphylococci may be present in the vagina or in nose or throat lesions or on the skin. If not present in the vagina itself, at the onset of menstruation the tampon may be contaminated by the user, thus introducing staphylococci and other organisms into the vagina. The word tampon, as used herein, means an absorptive body which may be used in any body cavity such as the vagina, a wound, or the like.

In addition, I have learned that dysmenorrhea is related to intra-vaginal and intrauterine infections and that both toxic shock syndrome and many cases of dysmenorrhea are prevented or alleviated by the inventive tampons to be described below which may incorporate the full range of substances that kill infections agents.

The blood, desquamated tissue and other materials present in the vagina during menstruation are an ideal culture medium for Staph. aureus and organisms symbiotic to staphylococci. The tampon may facilitate growth of the staphloccoccal infection. As the infection progresses, toxins are produced which are quickly absorbed into small abrasions and other entry points normally present in the vagina. These toxins may be absorbed in the cervix and the endometrium as well as the vagina. The resulting condition is toxic shock syndrome.

In accordance with the present invention a reliable technique for combating toxic shock syndrome is provided. The same is achieved without varying the routine of the user through the addition of additional procedures such as douches, alternation of different types of feminine napkins, or the like. Specifically, a protective method is integrated into the tampon procedure of the prior art by incorporating within the surface of the tampon an anti-staphlococcal agent. If a mechanical device integral with the tampon prior to use is used to insert the tampon, the mechanical device similarly incorporates a protective agent.

BRIEF DESCRIPTION OF THE DRAWINGS

Several ways of carrying out the invention are described in detail below with reference to the drawings, which only illustrate the invention, in which:

FIG. 1 is a perspective view of the inventive tampon;

FIG. 2 shows insertion of the inventive tampon; and

FIG. 2a is a perspective view of the absorptive tampon insert partially in cross-section.

FIG. 3 schematically illustrates fabrication of the inventive tampon.

BEST MODE FOR CARRYING OUT THE INVENTION

Referring to FIG. 1 in the present invention a tampon 10 comprising cylindrical tampon insert 12 is made of layered, woven, rolled or compressed fibrous material 14 having absorptive characteristics. The cylindrical insert itself has domed ends 16 also made of the absorptive material and longitudinal ridges 18 in the fibrous material at the circumferential surfacee of the insert. See FIG. 2(a). These contours increase the exposed surface area of the fibrous material in order to likewise increase the absorptive characteristics of the cylindrical insert. Attached to or protruding from one end of the cylindrical insert is a string 20 several inches in length. This string must be able to retain its strength when moistened, since in use pressure will be exerted on the string after it has been moistened.

The cylindrical insert is contained within a hollow cylinder 22 of larger diameter and longer length than the cylindrical insert. When properly positioned, the end 24 of the cylindrical insert which does not have the string attached to it is in close proximity to one of the open ends of hollow cylinder 22. The end of the cylindrical insert which has the string attached to it is then necessarily located at a point within the hollow cylinder not in close proximity to either end of the hollow cylinder. The hollow cylinder itself is made of non-absorptive material such as plastic, as is a plunger 26 which also fits snugly within the hollow cylinder. The plunger insert is fitted into the end 24 of the hollow cylinder which is not in close proximity to the end of the cylindrical insert. Plunger 26 incorporates a groove 27 which allows string 20 to extend out of the tampon 10. In its retracted position, illustrated in FIG. 1, the plunger insert is fitted snugly within the hollow cylinder with one end in close proximity to the end of the cylindrical insert located well within the hollow cylinder. In this position the length of the plunger results in the opposite end of the plunger protruding from the opening of hollow cylinder which is not in close proximity to either end of the cylindrical insert.

In its fully extended position (FIG. 2), the end of the plunger that was outside the end of the hollow cylinder is brought up within close proximity to the end of the hollow cylinder from which the plunger protruded in its retracted state. The end of the plunger which was located within the hollow cylinder in the retracted position is brought in close proximity to the other end of the hollow cylinder.

The outer circumferential surface of the cylindrical insert, the inner and outer circumferences of the hollow cylinder, and the exposed surface of the plunger are all covered with a povidone-iodine compound. The PVP (poly vinyl pyrrolidone) compound is a mixture containing poly vinyl pyrrolidone (PVP) powder and approximately 10% dry powdered iodine. The PVP is important only as a holding medium for the dry iodine. Therefore, other materials which will retain the iodine are useful. In addition, other elements more or less similar to iodine may be substituted.

This compound, and or others like it, can be in powdered form or suspended in water or in other suspending medium. If suspended in water an appropriate solution would be made by using appoximately 10% by weight of the compound. Additionally, the compound could be used in a gelatin form. One method of obtaining such a gelatin is to use one of the commercially available gelatins or pastes and also incorporating nitrofurazone. Various molecular weights of PVP can be used to provide antiseptic compounds of varying anitseptic action. This gelatinous form of the compound is particularly valuable in the invention as it is an effective vehicle for keeping the compound on the surface of the cylindrical tampon insert.

If the compound is used in liquid or gelatin form it would be desirable to hermetically seal the invention in a package containing an excess of the compound. If the compound is used in powdered form a hermetically sealed package may not be necessary. In the case of the powdered form of the compound it is sufficient to wrap the invention tightly in a cellophane-type packaging.

In manufacture, the fibrous material is tightly compressed to form the cylindrical shape. The material can be compressed by a tight rolling or weaving or by exerting other forms of pressure on the material. The PVP compound, or other like compounds is applied to the plunger insert, cylindrical insert, and hollow cylinder before or during assembly. In any of the states of the compound, namely, powder, liquid, or gelatin, it can be applied to the hollow cylinder, plunger insert, and cylindrical insert by several methods. The PVP compound can be sprayed or painted on these parts, or the parts can be rolled or immersed in the compound. In any of these methods an excess of the compound may be used to make up for loss due to unpackaging and handling immediately prior to use.

In the case of powdered compound, the tampon insert 12 may be fabricated forming a core 2 of absorptive fibers without the compound and forming the circumferential portion 30 of the tampon from a fibrous body having compound dispersal thoroughly throughout it. In this way the compound is kept at the surface of the tampon.

Referring to FIG. 3, this may be accomplished by bringing together two strands 32 of fiber saturated with compound. Strands 32 would be guided by suitable mechanical guides 34 into contact with a fiber strand 36 which does not contain compound. Strand 36 would be guided by guide 38 to meet strands 32. The guides would then wrap strands 32 around strand 36 to obtain the structure shown in FIGS. 1 and 2.

The cylindrical insert and the plunger are located within the hollow cylinder. This is accomplished by inserting the plunger into the hollow cylinder from the opposite end of the cylindrical cylinder from the cylindrical insert. Another method of assembly is to insert both the plunger and the cylindrical insert from the same end of the hollow cylinder. First the plunger is positioned within the hollow cylinder. Then, from the same end of the cylinder, the end of the cylindrical insert with the string attached is pushed toward the center of the hollow cylinder. Simultaneously, this forces the plunger into the proper retracted position. Once this assembly is complete, the invention is ready to be packaged. If the PVP or other antiseptic substance is in powdered form. This may simply mean rolling the invention in a cellophane-type wrapper. An excess of the powder may also be wrapped in the package. If a liquid or gelatin form of the PVP compound is used it may be desirable to hermetically seal the inventive tampon in an excess of the liquid or gelatin PVP compound.

In use, the invention is removed from its wrapper or hermetically sealed container, and is inserted into the vaginal vault. The end of the hollow cylinder with the cylindrical insert in close proximity to it, the forward end, is the end that is inserted first. After the full length of the hollow cylinder has been inserted into the vaginal vault the cylinder is slid with respect to the plunger in the conventional manner. This sliding of the plunger relative to the hollow cylinder forces the cylindrical insert to exit from the forward end of the hollow cylinder. Once the cylindrical insert has fully exited from the hollow cylinder and is properly positioned the hollow cylinder and plunger are removed from the vaginal vault to be discarded. The PVP compound on the hollow cylinder, plunger, and cylindrical insert dispenses within the vaginal vault. The antibiotic properties of the PVP compound prevent bacteria from being cultivated within the vaginal vault and thus prevents the development of toxins and toxic shock syndrome.

In my studies I have discovered that the use of coated tampons such as those described herein may on occasion produce untoward effects. It is my opinion that these effects, which generally involve an overgrowth of saprophytic or pathogenic organisms such as Candida albicans, are related to suppression of the normal organ flora by the antiseptic agents. I have discovered that this effect is minimized or eliminated by several methods such as:

1. Intermittent application of the invention with brief (twelve hour periods) intervals without the inventive tampon in place.

2. Measured dosages of the antiseptic compound, such as 1 ml. of Polyvinylpyrrolidone Iodine gel applied to the surface of the tampon.

3. Intermittent insertion of the invention coated with an innocuous suspension such as "yogurt", which contains micro-organisms that do not cause clinical disease.

4. Restriction of the use of the invention to periods of time not to exceed approximately twelve hours with the invention kept out of place during sleep.

5. Avoidence of the use of the invention in patients known medically to encourage, in their body tissues, the growth of saprophytic organisms. These include diabetes, the severely debilitated, those using potent anticarcinogens for the treatment of known cancer, those with lowered resistance due to the absence of antimicrobial substances due to inherent defects, and the like.

A benefit also occurs when these tampons are used in women who do not manifest toxic shock syndrome but who do manifest dysmenorrhea or other intravaginal-intra uterine disease. A benefit also occurs when these treated tampons are used in situations in which patients fail to benefit from the insertion of ordinary tampons or tampon-like devices in sites of injury or in body cavities where infection is a causal event or potential complication of injury or other disease.

ALTERNATIVE EMBODIMENT

In place of a compound made of only PVP and iodine, (in an appropriate carrier with preservative [such as "POVIDONE" which is commercially available]) different forms of antiseptic, antimicrobial, antifungal, antiviral, antiparasitic, or antibiotic compounds can be combined with the PVP. Examples of possible materials to be mixed with the PVP in place of or along with the iodine are mercury, zinc, penicillin, or erythromycin. One example of such an alternative embodiment is 2% nitrofurazone in a water miscible liquid such as glycerine, cetyl alcohol, mineral oil, ethoxylated fatty alcohol, methylparraben, or propylparafin. Other like compounds can be prepared using other elements such as fluoride, bromide, or the like, which combine readily with polyvinylpyrrolidone. In addition, certain metallic substances such as iron can be magnetized and can manifest antiseptic properties. Likewise, certain radioactive substances conventionally used for anti-cancer action also manifest antiseptic properties in the inventive tampon.

In summary, any of a wide variety of substances manifesting antiseptic action against any of the entire spectrum of pathogenic organisms can be incorporated into tampons for intravaginal use or for insertion into natural body cavities or cavities created artificially by surgical or non-surgical (accidental) events.

I claim:

1. A tampon comprising an elongated absorbing member having first and second ends and constructed of an absorptive material and incorporating a substance which kills pathogens within the surface or substance of said absorbing member, said member being housed within a smooth surfaced tubular container, having inner and outer surfaces, both the inner and outer surfaces of said tubular container being coated with said substance or the like.

2. A tampon as in claim 1 wherein a plunger is positioned within said cylindrical container at the opposite end of said cylindrical container from said absorbing member and axially aligned with said absorbing member.

3. A tampon as in claim 2 wherein said plunger is coated with said antibacterial compound, or the like.

4. A tampon as in claim 2 wherein said antibacterial compound consists of a mixture of polyvinylpyrrolidone as an absorptive agent and iodine as an antibacterial agent, said antibacterial agent dispersing from said cylindrical insert when said cylindrical insert comes in contact with body fluids.

5. A tampon as in claim 4 wherein said antibacterial compound contains zinc as an antibacterial agent.

6. A tampon as in claim 4 wherein said antibacterial compound contains mercury as an antibacterial agent.

7. A tampon as in claim 4 wherein said antibacterial compound contains penicillin as an antibacterial agent.

* * * * *